United States Patent [19]

Sebti et al.

[11] Patent Number: 5,705,686
[45] Date of Patent: Jan. 6, 1998

[54] INHIBITION OF FARNESYL TRANSFERASE

[75] Inventors: Said Sebti; Andrew Hamilton, both of Pittsburgh, Pa.

[73] Assignee: University of Pittsburgh, Pittsburgh, Pa.

[21] Appl. No.: 371,682

[22] Filed: Jan. 12, 1995

Related U.S. Application Data

[63] Continuation-in-part of Ser. No. 62,287, May 18, 1993, Pat. No. 5,602,098.
[51] Int. Cl.$^6$ .................. A61K 38/05; C07C 321/00; C07C 211/00
[52] U.S. Cl. .................. 562/557; 514/19; 564/308; 564/337
[58] Field of Search .................. 562/557; 514/19; 564/308, 337

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |

FOREIGN PATENT DOCUMENTS

| | | |
|---|---|---|
| 2072033 | 6/1992 | Canada . |
| 0203587 | 12/1986 | European Pat. Off. . |
| 0456180 | 11/1991 | European Pat. Off. . |
| 0461869 | 12/1991 | European Pat. Off. . |
| 0512865 | 11/1992 | European Pat. Off. . |
| 0520823 | 12/1992 | European Pat. Off. . |
| 0523873 | 1/1993 | European Pat. Off. . |
| 0528486 | 2/1993 | European Pat. Off. . |
| 0534546 | 3/1993 | European Pat. Off. . |
| 0535730 | 4/1993 | European Pat. Off. . |
| WO9116340 | 10/1991 | WIPO . |
| WO9218465 | 10/1992 | WIPO . |
| WO9409766 | 5/1994 | WIPO . |

OTHER PUBLICATIONS

Vogt, J Biol Chem 270, 660, 1995.
Sako, Chem Pharm Bull 40, 49, 1992.
Harrington, Biorg Med Chem Lett vol. 4, 2775, 1994.
Hancock et al, "A polybasic Domain or Palmitoylation is Required in Addition to the CAAX Motif to Localize p21$^{ras}$ to the Plasma Membrane", Cell, vol. 63, Oct. 5, 1990, pp. 133–139.
Reiss et al, "Inhibition of Purified p21$^{ras}$ Farnesyl:Protein Transferase by Cys–AAX Tetrapeptides", Cell, vol. 62, Jul. 13, 1990, pp. 81–88.
Willumsen et al, "The p21 ras C–terminus is required for transformation and membrane association," Nature, vol. 310, Aug. 16, 1984, pp. 583–586.

*Primary Examiner*—Cecilia J. Tsang
*Assistant Examiner*—David Lukton
*Attorney, Agent, or Firm*—Cushman Darby & Cushman IP Group of Pillsbury Madison & Sutro LLP

[57] ABSTRACT

A compound of the formula $$C^1R$$

where $C^1$ is 3-mercapto-2-amino-propylamino and R is an aryl group. The compounds are useful for inhibiting p21ras farnesyltransferase.

8 Claims, 5 Drawing Sheets

1

2

3

4a: R¹=COOH  R²=H
4b: R¹=H     R²=COOH
4c: R¹=CH₃   R²=H

Ras

Rap1A

INHIBITION OF FARNESYL TRANSFERASE

RELATED APPLICATION

The present application is a continuation-in-part of Ser. No. 08/062,287, filed May 18, 1993, now U.S. Pat. No. 5,602,098 the contents of which are incorporated herein by reference.

INTRODUCTION

The present invention relates to novel peptidomimetics which are useful as inhibitors of p21ras farnesyltransferase (FTase).

Cysteine farnesylation of the carboxyl terminal tetrapeptides CAAX (C=Cys, A=Leu, Ile or Val, X=Met or Ser) of the oncogene product Ras is required for its malignant transformation activity. As a consequence, farnesyltransferase (FTase), the enzyme responsible for the essential lipid modification, has become one of the most sought after targets for anticancer drug development. Previously, proposed peptide mimics have shown potent inhibition of FTase in vitro but have certain undesirable peptide features that hamper their use in vivo. The invention is concerned with non-peptide mimetics of CAAX which are free from peptide amide groups and other peptidic features which are effective and selective for FTase inhibition both in vitro and in vivo.

The invention was supported by grants from the National Cancer Institute (NIH).

BACKGROUND TO THE INVENTION

Ras is a small guanine nucleotide binding GTPase that transduces biological information from the cell surface to the nucleus (1). Its ability to transfer growth signals from receptor tyrosine kinases to a mitrogen activated protein (MAP) kinase cascade puts it in the heart of signaling pathways that cause proliferation in normal cells and uncontrolled growth in cancer cells (2). Indeed, mutations that lock ras in its active, GTP-bound state lead to malignant transformation and are among the most frequently identified mutations in human cancers (1). For example, 50% of colorectal and 95% of pancreatic human cancers have activated ras oncogenes.

Over the last decade, several strategies have been investigated, with only moderate success, to disrupt ras function and hence, to inhibit the growth of tumors with activated ras oncogenes. The search has recently intensified with the discovery that ras requires lipid modification with a farnesyl group for localization to the plasma membrane where it plays a pivotal role in growth signaling (3–9). Because farnesylation is required and sufficient for ras membrane association and transformation (10), the enzyme that catalyzes this lipid modification, farnesyltransferase (FTase), has become a major target for the design of novel anticancer agents (11, 12).

FTase is a α and β heterodimer that transfers farnesyl from farnesylpyrophosphate, a cholesterol biosynthesis intermediate, to the cysteine of proteins containing the carboxyl terminal sequence CAAX (where C is cysteine, A is an aliphatic amino acid and X is any amino acid except Leu or Ile) (13, 14). A closely related prenyltransferase, geranylgeranyltransferase I (GGTase I) catalyzes cysteine geranylgeranylation of proteins ending in CAAX where X - Leu or Ile (15, 16). In contrast to FTase and GGTase I, a third prenyltransferase, GGTase II, does not recognize CAAX sequences but rather geranylgeranylates proteins ending in CC or CXC sequences (15, 16). Prenylation of CAAX sequences by FTase and GGTase I is followed by proteolysis of the tripeptide AAX and carboxymethylation of the resulting prenylated cysteine, whereas GGTase II-catalyzed reactions are not followed by further posttranslational modifications. Since the number of geranylgeranylated proteins in the cell far exceeds that of farnesylated proteins (15, 16), it is critical that farnesylation inhibitors with potential anticancer activity be highly selective for FTase over GGTase I to minimize side effects.

Developing Ras CAAX tetrapeptide mimics as anticancer drugs has been prompted by the observation that FTase recognizes and farnesylates CAAX peptides which were also found to be potent competitive inhibitors of the enzyme $IC_{50s}$=50–200 nM) (13, 17–22). However, because of their peptidic nature, CAAX peptides do not inhibit Ras processing in whole cells. To enhance their poor cellular uptake and decrease their sensitivity to cellular proteases, it has been proposed to make CAAX pseudopeptides (23–25). Reduction of the amino terminal and central amide bonds of CAAX, and neutralization of the free carboxylate resulted in greater activity in whole cells (23–25).

Although the FTase inhibitors discussed above are potent inhibitors in vitro, they still retain several peptidic features which leave the proposed inhibitors vulnerable to proteolytic degradation in cells. With this in mind, it has been proposed in our copending parent U.S. application Ser. No. 08/062,287 to modify prior CAAX tetrapeptide mimics by, for example, replacing the peptide portion VI in CVIM, the carboxyl terminal of $K_D$-Ras, by a hydrophobic spacer such as 4-aminobenzoic acid (4-ABA) to link Cys to Met (i.e., Cys-4ABA-Met) (26–28). As an alternative, James et al (29) used a benzodiazepine group between cysteine and methionine. The latter suggested that the best disruption of FTase activity could be achieved when the inhibitors take up a β turn conformation that brings in close proximity the cysteine thiol and the methionine carboxylate to form a bidentate complex with a putative $Zn^{++}$ ion in the enzyme active site (29). However, conformational analysis of the inhibitor Cys-4ABA-Met described in Ser. No. 08/062,287, has shown that it could not take up a β-turn, arguing against this structural feature as a target for future FTase inhibitor design (27).

The compounds of Ser. No. 08/062,287 represent a significant improvement over prior FTase inhibitors. However, it is believed that even better results could be obtained if the amide bond or bonds or other peptidic features could be eliminated or at least reduced even further.

SUMMARY OF THE INVENTION

The principal object of the invention is to provide a group of non-peptide CAAX mimetics which contain no amide or hydrolyzable bonds. Basically these compounds comprise free cysteine thiol and terminal amino groups at one end and include a carboxylic acid or carboxylate group at the other end, the carboxylic acid or carboxylate group being separated from the cysteine thiol and terminal amino group by a hydrophobic spacer moiety which is free from any linking amido group as in prior CAAX mimetics. The present compounds are not subject to proteolytic degradation inside cells while retaining the structural features required for FTase inhibition. The compounds selectively inhibit FTase both in vitro and in vivo and offer a number of other advantages over prior CAAX peptide mimetics.

The compounds of the invention may be illustrated by the formula:

$C^1R$ where $C^1$ is 3-mercapto-2-amino-propylamino and R is an aryl group, notably biphenyl substituted with a —COOH group and/or lower alkyl, e.g., methyl. Preferably, R is biphenyl with —COOH substitution in the 3- or 4-position, most preferably the 3-position, with respect to the NH-aryl group. The —COOH substituent may appear as such or in pharmaceutically acceptable salt or ester form, e.g., as the alkali metal salt or methyl ester.

The features of the invention are illustrated herein by reference to the CAAX tetrapeptide known as CVIM (see EP 0461869 and U.S. Pat. No. 5,141,851) and C-4ABA-M which is disclosed in pending parent U.S. application Ser. No. 08/062,287. These compounds are, respectively, Cys-Val-Ile-Met and Cys-4 aminobenzoic acid-Met where Cys is the cysteine radical and Met is the methionine radical.

DESCRIPTION OF PREFERRED EMBODIMENTS

For ease of reference, the following abbreviations may be used in the present specification:

| | |
|---|---|
| FTase: | farnesyltransferase; |
| GGTase: | geranylgeranyltransferase; |
| SDS-PAGE: | sodium dodecyl sulfate polyacrylamide gel electrophoresis; |
| PBS: | phosphate-buffered saline; |
| CAAX: | tetrapeptides where C is cysteine, A is an aliphatic amino acid and X is any amino acid; |
| 4-ABA: | 4-aminomethylbenzoic acid; |
| DTT: | dithiothreitol; |
| FPP: | farnesylpyrophosphate; |
| GGPP: | geranylgeranylpyrophosphate. |

Figure 1:
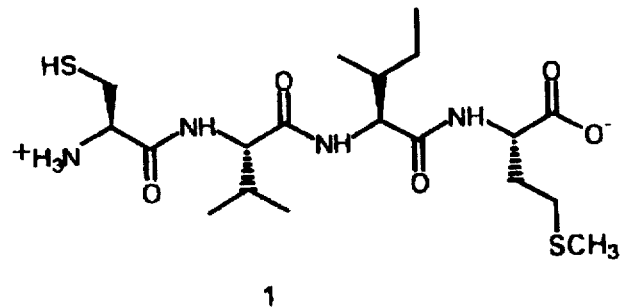
FIG. 1 illustrates the structures of previously disclosed peptidomimetics together with the compounds of the invention (4a, b and c)
Figure 1:
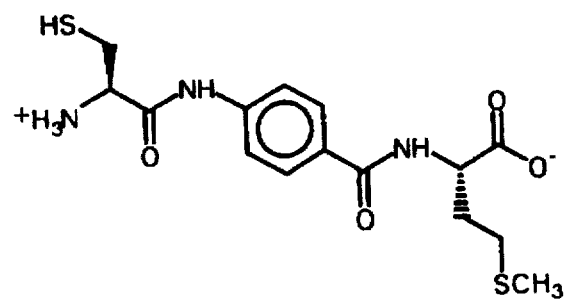
Figure 1:
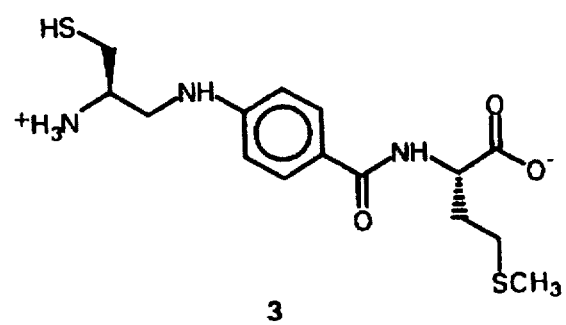
Figure 1:
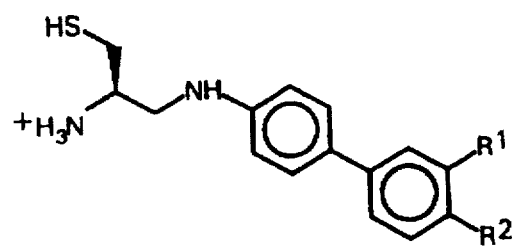

The preferred non-peptide CAAX mimetic of the invention is reduced cys-4-amino-3'-biphenylcarboxylate identified as 4a (FIG. 1). This derivative contains no amide bonds and thus is a true non-peptide mimic of the CAAX tetrapeptide.

Figure 2:
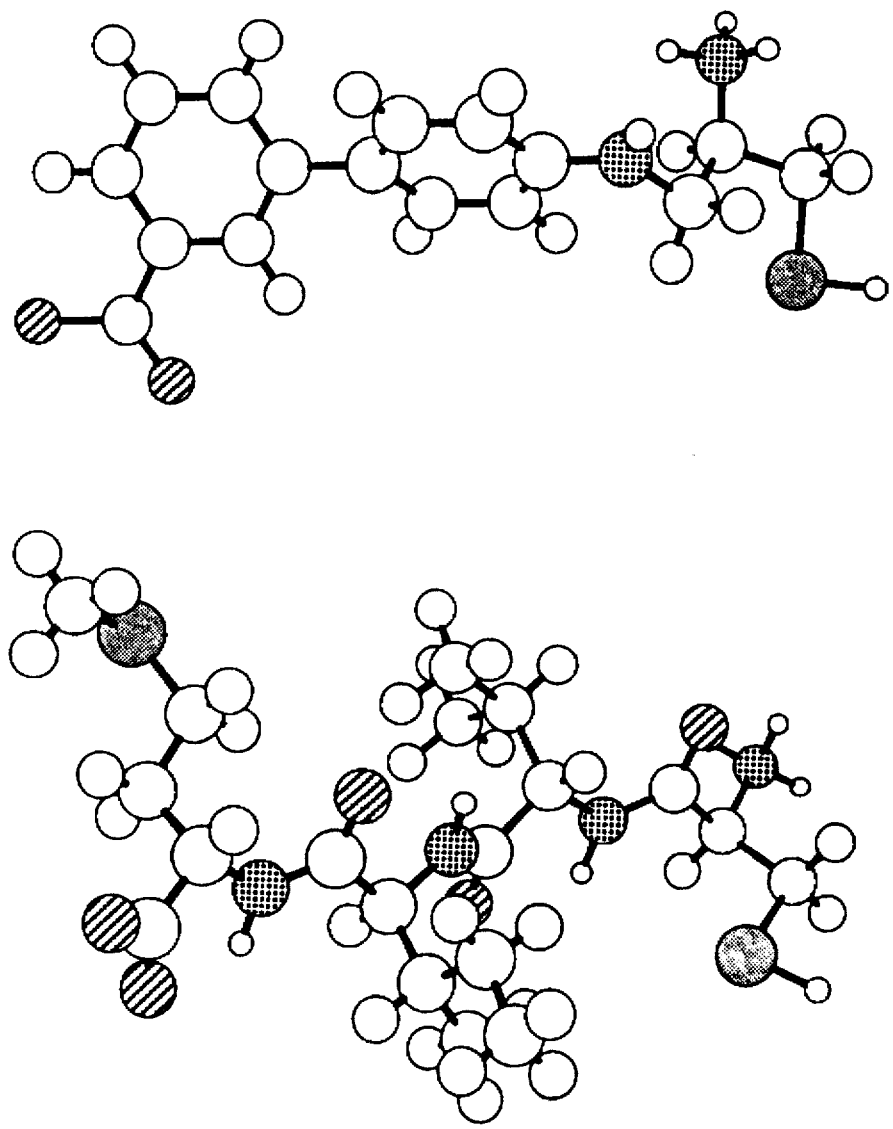
FIG. 2 illustrates the energy-minimized structural confirmations for CVIM and compound 4a of the invention.

Although 4a and compounds 1, 2 and 3 (FIG. 1) are structurally quite different, they share several features that are essential to FTase recognition. Most notably, they all have free cysteine thiol and terminal amino groups at the one end and carboxylate group on the other, these groups being separated by a hydrophobic moiety. Furthermore, molecular modeling studies indicate energy-minimized structures that show similar distances between the cysteine thiol and the free carboxylate in both (4a) and CVIM in the extended conformation (FIG. 2).

Compounds (4) and (4c) are also representative of the invention. While these compounds are somewhat less active than (4a), their overall properties indicate effectiveness as FTase inhibitors.

The compounds of the invention may be prepared using procedures which are conventional in the art. For example, compounds (4a) and (4b) of FIG. 1 may be prepared by reductive amination of 4-amino-3'-tert.butoxy-carbonyl biphenyl or 4-amino-4'-tert.butoxy carbonyl biphenyl, respectively, with N-Boc-S-trityl cysteinal followed by deprotection with, for example, trifluoroacetic acid and purification.

The compounds of the invention may be used in the carboxylic acid form or as pharmaceutically acceptable salts or esters thereof. Lower alkyl esters are preferred although other ester forms, e.g., phenyl esters, may also be used.

The compounds of the invention may be used in the same manner as prior CAAX tetrapeptide inhibitors to inhibit p21ras farnesyltransferase in any host containing the same. This includes both in vitro and in vivo use. Because the compounds inhibit farnesyltransferase, notably human tumor p21ras farnesyltransferase, and consequently inhibit the farnesylation of the oncogene protein ras, they may be used in the treatment of cancer or cancer cells. It is noted that many human cancers have activated ras and, as typical of such cancers, there may be mentioned colorectal carcinoma, myeloid leukemias, exocrine pancreatic carcinoma and the like.

The compounds of the invention may be used in pharmaceutical compositions of conventional form suitable for oral, subcutaneous, intravenous, intraperitoneal or intramuscular administration to a mammal or host. This includes, for example, tablets or capsules, sterile solutions or suspensions comprising one or more compounds of the invention with a pharmaceutically acceptable carrier and with or without other additives. Typical carriers for tablet or capsule use include, for example, lactose or corn starch. For oral compositions, aqueous suspensions may be used with conventional suspending agents, flavoring agents and the like.

The amount of inhibitor administered to obtain the desired inhibitory effect will vary but can be readily determined. For human use, daily dosages are dependent on the circumstances, e.g., age and weight. However, daily dosages of from 0.05 to 20 mg per kg body weight may be mentioned for purposes of illustration.

The invention is illustrated but not limited by the following examples:

EXAMPLE 1

The compound C-4ABA-Met of formula (2) (see FIG. 1) was prepared as described in reference (27). The protected form of the peptidomimetic (3) was prepared through the reductive amination of 4-aminobenzoyl methionine methyl ester and N-Boc-S-trityl cysteinal in methanol solution containing NaBH₃CN and 5% acetic acid. This reaction gave the N-Boc-S-trityl, methyl ester of (3) with a yield of 65%. The protected peptidomimetic was deesterified by LiOH in THF and then deprotected by trifluoroacetic acid in methylene chloride with two equivalents of triethylsilane to give crude (3) which was purified by reverse phase HPLC. The biphenyl-based peptidomimetic (4c) was prepared by the reductive amination of 4-amino-3'-methyl biphenyl with N-Boc-S-trityl cysteinal, to give the N-Boc-S-trityl derivatives of (4c), which was then deprotected by trifluoroacetic acid and purified by reverse phase HPLC. The peptidomimetics (4a) and (4b) were prepared from the reductive amination of 4-amino-3'-tert.butoxycarbonyl biphenyl and 4-amino-4'-tert.butoxycarbonylbiphenyl, respectively, with N-Boc-S-trityl cysteinal, to give the N-Boc-S-trityl, tert-butyl ester of (4a) and (4b). Deprotection by trifluoroacetic acid and purification by reverse phase HPLC gave pure (4a) and (4b).

The key intermediate 4-nitro-3'-methylbiphenyl was prepared from 1-bromo-4-nitrobenzene and 1-bromo-3-methylbenzene by Suzuki coupling reaction (30). The oxidation of 4-nitro-3'-methylbiphenyl by $KMnO_4$ gave 4-nitro-3'-biphenylcarboxylate, which was esterified to give the tert-butyl ester. The nitro group was reduced by palladium catalyzed hydrogenation to give the 4-amino-3'-tert-butoxycarbonylbiphenyl, the key intermediate for the reductive amination reaction. All compounds were more than 98% pure as determined by reverse phase HPLC, and their spectroscopic data were consistent with the assigned structures.

EXAMPLE 2

The potency of the peptidomimetics of FIG. 1 to inhibit partially purified FTase was evaluated by determining their ability to inhibit the transfer of farnesyl to recombinant H-Ras as described below. The results obtained showed that compound (2), i.e. Cys-4ABA-Met (1–10 µM) inhibited FTase in a concentration-dependent manner with an $IC_{50}$ of 150 nM (Table 1 below). This value is similar to the previously reported $IC_{50}$ values for CVIM and Cys-4ABA-Met (27). Reduction of the amide bond between cysteine and aminobenzoic acid gave the red-Cys-4ABA-Met (3) which had an $IC_{50}$ of 300 nM. However, replacing the methionine and the C-terminal amide bond in (3) by another aromatic ring to obtain the biphenyl-based peptidomimetic (4a) improved potency by twofold (Table 1). Peptidomimetic (4a) had an $IC_{50}$ of 150 nM towards partially purified FTase from human Burkitt lymphoma cells and 50 nM towards rat brain FTase purified to homogeneity. Thus, despite major structural differences between the compound CVIM (1) and (4a), the latter (4a) retained the potent FTase inhibitory activity of the tetrapeptide CVIM (1) and the peptide mimetics (2) and (3) (Table 1). This is significant because (4a), being free of any amide bonds, is significantly less subject to degradation in vivo.

Figure 3A:
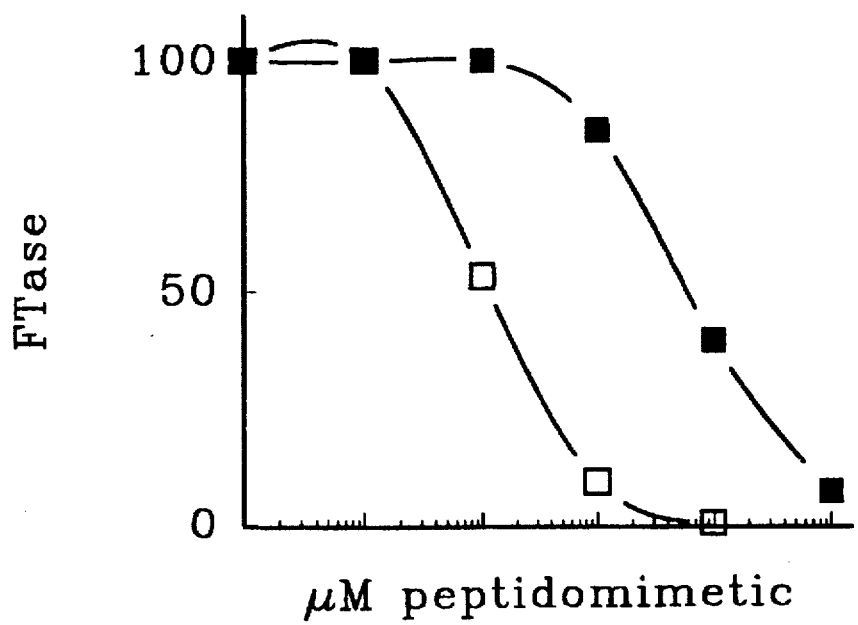
FIGS. 3A and B graphically illustrate the results of FTase and GGTase I inhibition studies.

The results obtained indicate that the position of the free carboxylate group is critical to FTase inhibition since placing this group at the 4'-position as in (4b) (FIG. 1) dramatically decreased its affinity towards FTase (see FIGS. 3A and Table 1). Thus, peptidomimetic (4b) ($IC_{50}$=6650 nM) was 45-fold less potent than its isomer (4a). This strongly suggests that within the active site of FTase, there must be a positively charged residue such as Lys with a precise spatial orientation to interact with the negative charge of the free carboxylate.

Replacing the 3'-carboxylate of (4a) with a methyl group as in (4c) also decreased potency but only by 5-fold ($IC_{50}$= 765 nM). This indicates that the FTase binding site prefers a neutral group at the 3'-position to a negative charge at the 4'-position suggesting either steric hindrance or repulsive interactions from the microenvironment surrounding the 4'-region of the biphenyl.

Notwithstanding the lower activity for (4b) and (4c), these compounds still offer in vivo advantages in view of their freedom from any amide group.

TABLE 1

| Compound | $IC_{50}$ (nM) | |
|---|---|---|
| | FTase | GGTase I |
| 2 | 150 | 1,500 |
| 3 | 300 | 4,400 |

TABLE 1-continued

| Compound | $IC_{50}$ (nM) | |
|---|---|---|
| | FTase | GGTase I |
| 4a | 150 | 100,000 |
| 4b | 6,650 | >100,000 |
| 4c | 765 | >100,000 |

The $IC_{50}$ values given in the Table 1 represent inhibition of FTase and GGTase I in vitro by the listed compounds. The data shown represent the average of at least two independent experiments.

The above results indicate that the tripeptide AAX is not essential for strong binding and all that is required for recognition is a hydrophobic scaffold with free thiol, amino and carboxylate groups held at precise positions. As noted earlier, a previous proposal (29, 33) suggested that potent inhibitory activity towards FTase might require inhibitors to take up a β turn conformation bringing the cysteine thiol and free carboxylate in close proximity to form a bidentate complex with $Zn^{++}$. However, the biphenyl-based non-peptide CAAX mimetic described here cannot take up this conformation (FIG. 2) thus leading to the conclusion that potent inhibition of FTase does not require β turn conformation.

Figure 3B:
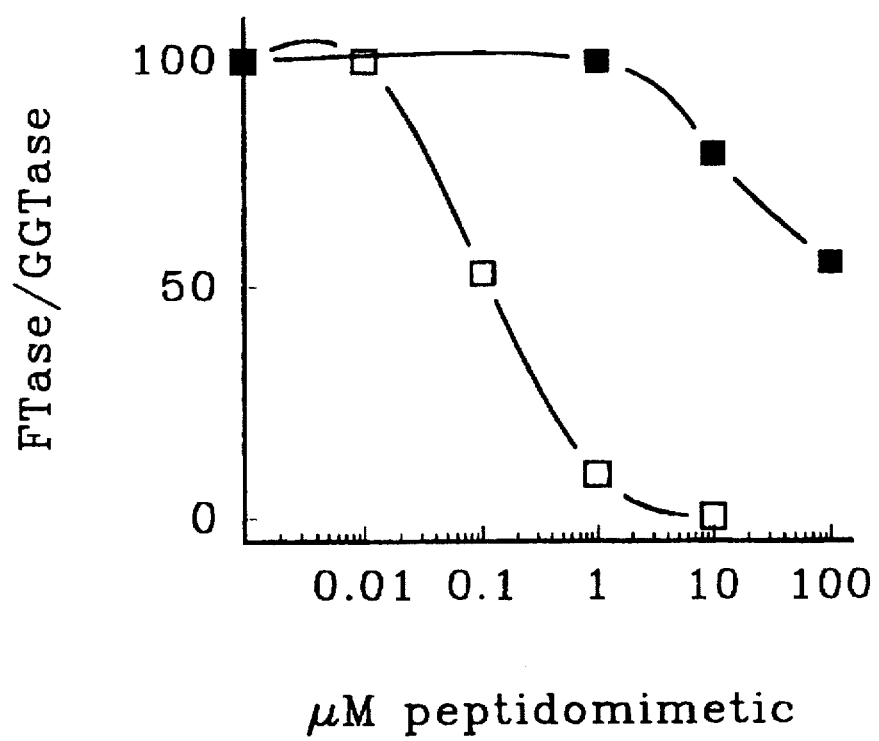

As noted, FIGS. 3A and 3B graphically illustrate the results of FTase and GGTase I inhibition studies. In these studies, partially purified FTase and GGTase I were incubated with the peptidomimetics to be tested and their ability to transfer [$^3$H] farnesyl to H-Ras-CVLS (FTase) and [$^3$H] geranylgeranyl to H-Ras CVLL (CCTase I) was determined as described below. FIG. 3A shows FTase inhibition by: □, (4a) and ■, (4b) while FIG. 3B plots FTase (□) and GGTase I (■) inhibition by (4a). Each curve is representative of at least four independent experiments.

Geranylgeranylation is a more common protein prenylation than farnesylation (15). It is, therefore, critical for useful CAAX peptidomimetics to have high selectivity towards inhibiting FTase in order to minimize side effects. In the CAAX tetrapeptides, the X position determines whether the cysteine thiol will be farnesylated by FTase or geranylgeranylated by GGTase I. Those proteins or peptides with Leu or Ile at the X position are geranylgeranylated. The present compounds do not significantly inhibit GGTase I and demonstrate much greater selectivity for FTase. See Table (1).

FIG. 3B shows that (4a), which is the most potent FTase inhibitor of the present compounds, is a very poor GGTase I inhibitor. The ability of (4a) to inhibit the transfer of geranylgeranyl to Ras-CVLL ($IC_{50}$=100,000 nM) was found to be 666-fold less than that of (4a) to inhibit the transfer of farnesyl to Ras-CVLS ($IC_{50}$=150 nM) (Table 1). This selectivity was much more pronounced than in the peptidomimetics (2) and (3) which were more selective for FTase relative to GGTase I by only 10 and 15-fold, respectively, (Table 1). It is also noted that the free carboxylate of (4a) is not responsible for this selectivity since replacement of this group by a methyl (4c) did not increase affinity towards GGTase I (Table 1). These results indicate that the FTase and GGTase I binding sites are quite different and that differences between Leu, Ile and Met side chains cannot be the only predictors of selectivity. Regardless of the explanation, it is clear that the compounds of the invention are much more selective to inhibition of FTase.

Figure 4:
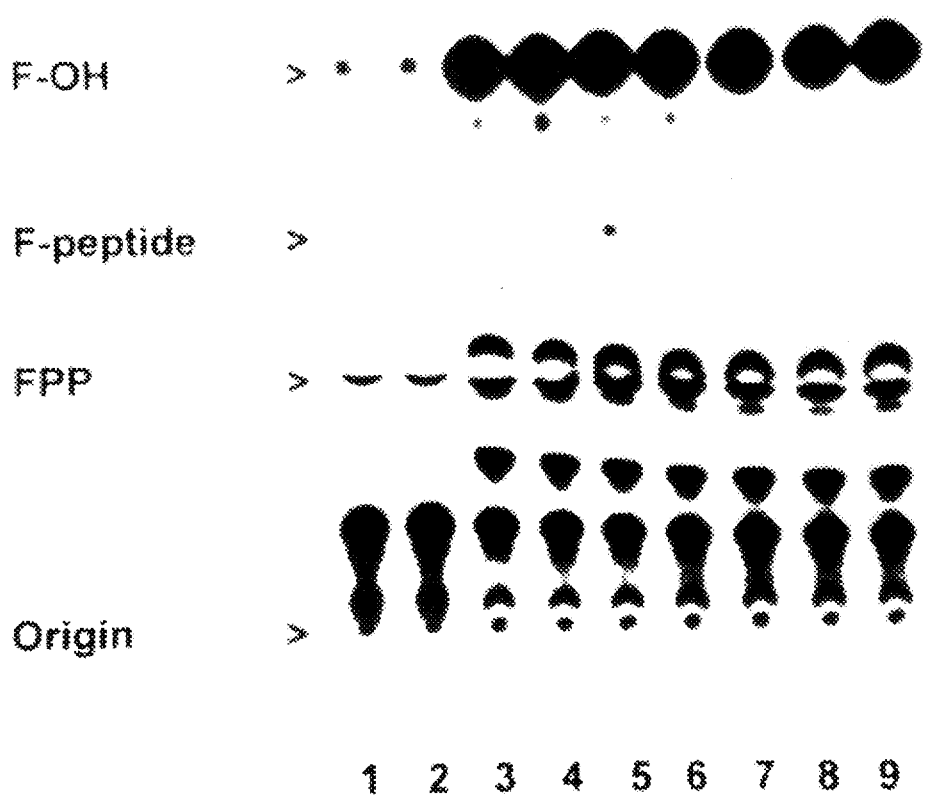
FIG. 4 is a silica gel TLC relating to Ras CAAX peptide and pepidomimetic farnesylation.

Besides having poor cellular uptake and being rapidly degraded, another disadvantage of natural CAAX peptides is that they are farnesylated by FTase. This results in metabolic inactivation since farnesylated CAAX derivatives are no longer inhibitors of FTase (26). FIG. 4 shows that the natural peptide CVLS (carboxyl terminal CAAX of H-Ras) is farnesylated by FTase from Burkitt lymphoma cells. Replacing the tripeptide VLS with 4-amino-3'-hydroxycarbonylbiphenyl, as in (4a) did not affect potency towards FTase inhibition (Table 1) but prevented farnesylation of the cysteine thiol (FIG. 4). None of the peptidomimetics of the invention is metabolically-inactivated by FTase (FIG. 4). Thus, although AAX tripeptides are not necessary for potent FTase inhibition, they appear to be required for farnesylation. This is in marked contrast to the present compounds.

With reference to FIG. 4, it is to be noted that the transfer of [$^3$H] farnesyl to peptides and peptidomimetic by FTase was determined by silica G TLC as described below. FPP, F-peptide, and ORIGIN designate farnesyl pyrophosphate, farnesylated peptide and origin, respectively. FIG. 4 shows: Lane 1, FPP only; lane 2, FPP and CVLS but no FTase; lane 3, FPP and FTase but not peptide. Lanes 4–9 all contained FTase and FPP with lane 4, VCIM; lane 5, CVLS; lane 6, compound 3; lane 7, compound (4a); lane 8, compound (4b); lane 9, compound (4c). The results shown indicate that the compounds of the invention are not farnesylated in contrast to the CAAX compounds. Data given are representative of two independent experiments.

Figure 5A:
FIGS. 5A-5B illustrates Ras and Rap1A processing in cells using a compound according to the invention.

The foregoing results show that the novel peptidomimetics described herein have three very important features, namely, they are potent FTase inhibitors, very poor inhibitors of the closely related GGTase I (and, therefore, selective to FTase inhibition) and they are resistant to metabolic inactivation by FTase. Another important feature is that the present compounds inhibit Ras processing in whole cells and retain their selectivity towards FTase in vivo. This is shown by the following with reference to FIG. 5 which illustrates Ras and Rap1A processing. To this end, Ras transformed 3T3 cells were treated with inhibitors, lysed and the lysate A) immunoprecipitated with anti-Ras antibody or B) separated by SDS-PAGE. Immunoprecipitates from A) were separated by SDS-PAGE and blotted with anti-Ras antibody whereas samples from B) were blotted with anti-Rap1A antibody as described hereafter. FIG. 5 shows: Lane 1, control; lane 2, lovastatin; lane 3, reduced (3) (200 µM); lane 4, (4a) (100 µM); lane 5, (50 µM); lane 6, (4a) (25 µM); lane 7, (4b); lane 8, (4c). Data are representative of 3 independent experiments. Farnesylated Ras runs faster than unprocessed Ras on SDS-PAGE (23–25, 28, 29). FIG. 5A (lane 1) shows that cells treated with vehicle contain only processed Ras whereas cells treated with lovastatin (lane 2) contained both processed and unprocessed Ras indicating that lovastatin inhibited Ras processing. Lovastatin, an HMG-CoA reductase inhibitor which inhibits the biosynthesis of farnesylpyrophosphate and geranylgeranylpyrophosphate, is used routinely as a positive control for inhibition of processing of both geranylgeranylated and farnesylated proteins (23–25, 28, 29). Cells treated with reduced Cys-4ABA-Met 3 in its free carboxylate forms did not inhibit Ras processing. However, in contrast, the corresponding methyl ester of (3) (200 µM) inhibited FTase (FIG. 5A, lane 3). This is consistent with previous work that showed that neutralization of the carboxylate of CAAX peptides enhances their ability to inhibit Ras processing (23, 25, 29). Although compound (4a) has a free carboxylate negative charge, it was able to enter cells and potently inhibit Ras processing (lane 4, 100 µM, 4a). It was found that compound (4a) inhibited Ras processing with concentrations as low as 50 µM (lane 5), whereas its corresponding parent compound (3) did not inhibit Ras processing at concentrations as high as 200 µM. Compound (4a) was as potent as the methylester of its parent compound (3) (FIG. 5A, lane 3). Furthermore, (4a) appears to be the first CAAX peptidomimetic that effectively inhibits Ras processing in whole cells directly without relying on cellular enzymes for activation. The hydrophobic character of the biphenyl group apparently compensates for the free carboxylate negative charge thus allowing the peptidomimetic to penetrate membranes and promoting its cellular uptake. Peptidomimetics (4b) and (4c) were not able to inhibit Ras processing (FIG. 5A, lanes 7 and 8).

Figure 5B:
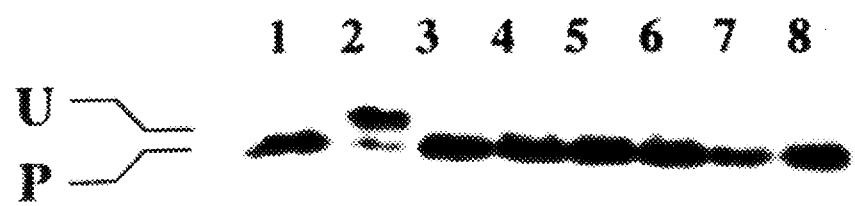

The selectivity of the present Ras farnesylation inhibitors has also been investigated by determining their ability to inhibit processing of Rap1A, a small G-protein that is geranylgeranylated (15, 16). Cells were treated with lovastatin or peptidomimetics exactly as described for Ras processing experiments. Lysates were then separated by SDS-PAGE and immunoblotted with anti-Rap1A antibody as described below. Control cells contained only the geranylgeranylated Rap1A (FIG. 5B, lane 1) whereas lovastatin-treated cells contained both processed and unprocessed forms of Rap1A indicating, as expected, that lovastatin inhibited the processing of Rap1A (FIG. 5B, lane 2). Compound (4a), which inhibited Ras processing, was not able to inhibit Rap1A geranylgeranylation (FIG. 5B, lanes 4–6). Compounds (4b) and (4c) also did not inhibit Rap1A processing (FIG. 5B, lanes 7 and 8).

In summary, the foregoing results show that the present compounds, which are characterized by their freedom from hydrolyzable groups and other peptidic features, demonstrate effective FTase inhibition while offering other advantages such as selective inhibition of farnesylation relative to geranylgeranylation, both in vitro and in vivo and freedom from metabolic inactivation by FTase.

The various assays referred to above were carried out as follows:

FTase and GGTase I Activity Assay

Human Burkitt lymphoma.(Daudi) cells (ATCC, Rockville, Md.) were grown in suspension in RPMI 1640 medium containing 10% fetal bovine serum (FBS) and 1% Pen-Strep in a humidified 10% $CO_2$ incubator at 37° C. The cells were harvested and sonicated in 50 mM Tris, pH 7.5, 1 mM EDTA, 1 mM EGTA, 25 µg/ml leupeptin, 1 mM phenylmethylsulfonyl fluoride. Homogenates were then spun at 12,000×g and the resulting supernatant further spun at 60,000×g. The supernatant was assayed for both FTase and GGTase I. Briefly, 100 µg of the supernatants was incubated in 50 mM Tris, pH 7.5, 50 µM $ZnCl_2$, 20 mM KCl, 3 mM $MgCl_2$ and 1 mM DTT. For FTase assays, the reaction was incubated at 37° C. for 30 minutes with recombinant H-Ras-CVLS (11 µM) and [$^3$H] FPP (625 nM; 16.3 Ci/mmol). For GGTase assays, the reaction was also incubated for 30 minutes at 37° C. but with recombinant H-Ras-CVLL (5 µM) and [$^3$H] GGPP (525 nM; 19.0 Ci/mmol). The reaction was stopped and passed through glass fiber filters to separate free and incorporated label. For inhibition studies, the peptidomimetics were premixed with FTase or GGTase I prior to adding the remainder of the reaction mixture. Recombinant H-Ras-CVLS was prepared as described previously (26) from bacteria (31). Recombinant H-Ras-CVLL was prepared from bacteria (32).

Peptidomimetics Farnesylation Assay

The ability of human Burkitt lymphoma (Daudi) FTase to farnesylate peptides and peptidomimetics was determined as described previously (26, 27). Briefly, 25 μl of reaction mixture containing 50 μg of 60,000×g supernatants and 20 μM peptidomimetic in 50 mM Tris, pH 7.5, 50 μM ZnCl$_2$, 20 mM KCl, 3 mM MgCl$_2$, 1 mM DTT and 0.2% octylβ-D-glucoside was incubated for 30 minutes at 37° C., then spotted onto silica gel G TLC sheets (20×20 cm, Brinkmann Instruments), and developed with n-propanol/5N ammonium hydroxide/water (6:1:1). The dried sheets were sprayed with En$^3$Hance (DuPont NEN) and exposed to x-ray film for detection of [$^3$H] farnesylated products.

Ras and Rap1A Processing Assay

EJ3 cells were treated with peptidomimetics or vehicle for 20–24 h. Cells were lysed in lysis buffer (10 mM Na$_2$HPO$_4$, pH 7.25, 150 mM NaCl, 0.1% sodium dodecyl sulfate, 1% Triton X-100, 12 mM sodium deoxycholate, 1 mM NaF, 0.2% NaN$_3$, 2 mM PMSF, 25 μg/ml leupeptin) and the lysates were cleared by spinning at 13,000 rmp for 15 minutes. Ras protein was immunoprecipitated overnight at 4° C. with 50 μg of anti-Ras antibody (Y13-259; hybridoma from ATCC, Rockville, Md.) along with 30 μl Protein A-agarose goat anti-rat IgG complex (Oncogene Science, Uniondale, N.Y.). Immunoprecipitates were washed 4 times with lysis buffer and the bound proteins were released by heating for 5 minutes in 40 μl SDS-PAGE sample buffer and subsequently electrophoresed on a 12.5% SDS-PAGE. Proteins were transferred onto nitrocellulose and subsequently blocked with 5% non-fat dry milk in PBS (containing 1% Tween 20 (PBS-T) and probed with Y13-259 (50 μg/ml in 3% non-fat dry milk in PBS-T). Positive antibody reactions were visualized using peroxidase-conjugated goat anti-rat IgG (Oncogene Science, Uniondale, N.Y.) and an enhanced chemiluminescence detection system (ECL; Amersham).

For Rap1A processing assays, 50 μg of cell lysates were electrophoresed as described above for Ras processing and transferred to nitrocellulose. These membranes were then blocked with 5% milk in Tris-buffered saline, pH 8.0, containing 0.5% Tween-20 and probed with anti-Rap1A (1 μg/ml in 5% milk/TBS-T; Santa Cruz Biotechnology, Santa Cruz, Calif.). Antibody reactions were visualized using peroxidase-conjugated goat anti-rabbit IgG (Oncogene) and ECL chemiluminescence as described above.

Structural Modeling (FIG. 2)

The calculation of the energy minimized conformations was carried out using the AMBER force field within the MacroModel program, version 3.5a.

References

Literature references mentioned above are more specifically identified as follows:

1. Barbacid, M., *Annu. Rev. Biochem.*, 56:779–929 (1987)
2. McCormick, F., *Nature*, 363:15–16 (1993)
3. Willumsen et al, *Nature*, 310:583–588 (1984)
4. Willumsen et al, *EMBO J.*, 3:2581–2585 (1984)
5. Hancock et al, *Cell*, 57:1167–1177 (1989)
6. Gutierrez et al, *EMBO J.*, 8:1093–1098 (1989)
7. Casey et al, *Proc. Natl. Acad. Sci. U.S.A.*, 86:8323–8327 (1989)
8. Jackson et al, *Proc. Natl. Acad. Sci. U.S.A.*, 87:3042–3046 (1990)
9. Hancock et al, *Cell*, 63:133–139 (1990)
10. Kato et al, *Proc. Natl. Acad. Sci. U.S.A.*, 89:6403–6407 (1992)
11. Gibbs, J. B., *Cell*, 65:1–4 (1991)
12. Gibbs et al, *Cell*, 77:175–178 (1994)
13. Reiss et al, *Cell*, 63:81–88 (1990)
14. Reiss et al, *J. Biol. Chem.*, 266:10672–10877 (1991)
15. Casey, P., *J. Lipid. Res.*, 88:1731–1740 (1992)
16. Cox et al, *Curr. Op. Cell Biol.*, 4:1008–1016 (1992)
17. Reiss et al, *Proc. Natl. Acad. Sci. U.S.A.*, 88:732–736 (1991)
18. Manne et al, *Proc. Natl. Acad. Sci. U.S.A.*, 87:7541–7545 (1990)
19. Moores et al, *J. Biol. Chem.*, 266:14603–14610 (1991)
20. Goldstein et al, *J. Biol. Chem.*, 266:15575–15578 (1991)
21. Brown et al, *Proc. Natl. Acad. Sci. U.S.A.*, 89:8313–8316 (1992)
22. Pompliano et al, *Biochemistry*, 31:3800–3807 (1992)
23. Kohl et al, *Science*, 260:1934–1937 (1993)
24. Graham et al, *J. Med. Chem.*, 37:725–732 (1994)
25. Garcia et al, *J. Biol. Chem.*, 268:18415–18418 (1993)
26. Nigam et al, *J. Biol. Chem.*, 268:20695–20698 (1993)
27. Qian et al, *J. Biol. Chem.*, 269:12410–12413 (1994)
28. Qian et al, *Bioorg. Med. Chem. Lett.*, 4:2579–2584, (1994)
29. Goldstein et al, *Science*, 260:1937–1942 (1993)
30. Watanabe et al, *Syn. Lett.*, 3:207–210 (1992)
31. Lacal et al, *Proc. Natl. Acad. Sci. U.S.A.*, 81:5305–5309 (19840
32. Cox et al, *Mol. Cell. Biol.*, 12:2606–2615 (1992)
33. Stradley et al, *Biochemistry*, 32:12586–12590 (1993)

It will be appreciated that various modifications may be made in the invention as described above without departing from the scope and intent thereof as defined in the following claims wherein:

We claim:

1. A compound of the formula $C^1R$ where $C^1$ is 3-mercapto-2-amino-propylamino and R is biphenyl, optionally substituted with a carboxyl and/or alkyl moiety; or a pharmaceutically acceptable salt thereof.

2. A compound according to claim 1 wherein R is a biphenyl group substituted with —COOH.

3. A compound according to claim 1 wherein R is a biphenyl group substituted with lower alkyl.

4. A compound according to claim 3 wherein the lower alkyl is methyl.

5. A compound according to claim 1 of the formula:

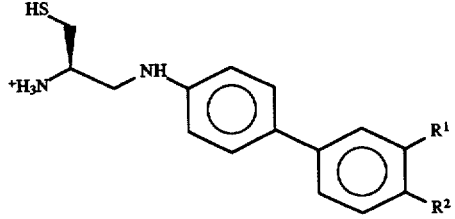

where $R^1$ is hydrogen, COOH or CH$_3$; and
$R^2$ is hydrogen or COOH, $R^1$ being COOH or CH$_3$ when $R^2$ is hydrogen.

6. A compound according to claim 5 wherein $R^1$ is COOH and $R^2$ is hydrogen.

7. A method of inhibiting p21ras farnesyltransferase in a host in need of such inhibition which comprises administering to said host an effective amount of a compound according to claim 1.

8. A pharmaceutical composition comprising a compound according to claim 1 and a pharmaceutically acceptable carrier therefor.

* * * * *